United States Patent [19]

Viswanathan et al.

[11] Patent Number: 5,705,728
[45] Date of Patent: Jan. 6, 1998

[54] PROCESS FOR THE PRODUCTION OF ETHYLENE AND MIXTURE CONTAINING ETHYLENE

[75] Inventors: Krishnan Viswanathan, Grand Island; Hang-Chang Bobby Chen, Getzville, both of N.Y.; Sidney W. Benson, Los Angeles, Calif.

[73] Assignee: Occidental Chemical Corporation, Dallas, Tex.

[21] Appl. No.: 388,175

[22] Filed: Feb. 10, 1995

Related U.S. Application Data

[63] Continuation of Ser. No. 190,434, Feb. 2, 1994, abandoned, which is a continuation of Ser. No. 41,534, Apr. 1, 1993, abandoned, which is a continuation of Ser. No. 622,239, Dec. 6, 1990, abandoned.

[51] Int. Cl.$^6$ .............................. C07C 1/30; C07C 5/00; C07C 17/00
[52] U.S. Cl. .................... 585/641; 585/638; 585/654; 585/656; 585/657; 585/658; 570/101; 570/181; 570/216; 570/230
[58] Field of Search .................... 585/654, 657, 585/659, 638, 641, 658; 570/101, 181, 216, 230

[56] References Cited

U.S. PATENT DOCUMENTS

| | | | |
|---|---|---|---|
| 2,259,195 | 10/1941 | Baehr et al. | 260/680 |
| 2,488,083 | 11/1949 | Gorin et al. | 260/677 |
| 2,628,259 | 2/1953 | Dirstine | 260/654 |
| 2,838,579 | 6/1958 | Conrad et al. | 260/662 |
| 2,890,253 | 6/1959 | Mullineaux et al. | 260/673.5 |
| 3,166,601 | 1/1965 | Taylor | 260/654 |
| 3,173,962 | 3/1965 | Carroll et al. | 260/659 |
| 3,207,811 | 9/1965 | Bajars | 260/680 |
| 3,557,229 | 1/1971 | Riegel | 260/656 |
| 3,558,735 | 1/1971 | Beard, Jr. | 260/683.3 |
| 3,658,934 | 4/1972 | Beard | 260/683.3 |
| 3,702,311 | 11/1972 | Beard, Jr. | 252/441 |
| 3,862,996 | 1/1975 | Beard | 260/677 XA |
| 4,102,935 | 7/1978 | Kroenke et al. | 260/656 R |
| 4,102,936 | 7/1978 | Magistro | 260/656 R |
| 4,119,570 | 10/1978 | Kroenke et al. | 252/466 J |
| 4,217,311 | 8/1980 | Zaidman et al. | 260/656 R |
| 4,300,005 | 11/1981 | Li | 570/224 |
| 4,375,569 | 3/1983 | Kroenke et al. | 570/224 |
| 4,461,919 | 7/1984 | Kroenke et al. | 570/224 |
| 4,467,127 | 8/1984 | Kroenke et al. | 570/224 |

FOREIGN PATENT DOCUMENTS

| 2095242 | of 0000 | United Kingdom | C07C 21/06 |
|---|---|---|---|
| 2095245 | of 0000 | United Kingdom | C07C 21/06 |

*Primary Examiner*—Ponnathapura Achutamurthy

[57] ABSTRACT

The present invention provides an efficient process for the production of ethylene or a mixture of ethylene and vinyl chloride, in which some 1,2-dichloroethane (EDC) may also be produced, by reacting chlorine with ethane. The process is characterized by a conversion of ethane per pass through the reactor of at least about 50%, and a combined molar yield of ethylene and vinyl chloride of at least about 80% based on the ethane consumed. In accordance with this invention, there is provided a process for preparing ethylene or a mixture of ethylene and vinyl chloride by the reaction of ethane and chlorine which comprises:

(a) providing a stream of ethane feed gas and a stream of chlorine feed gas;
(b) preheating either said ethane stream only or both said ethane and chlorine streams;
(c) thoroughly mixing said ethane and chlorine feed gases within about one second and at a molar ratio of ethane to chlorine of at least about 0.9:1.0;
(d) said preheating being sufficient to enable the resultant mixture to have a temperature above the free radical formation temperature for chlorine; and
(e) permitting said ethane and chlorine in said mixture to react so that the reacted mixture has a temperature between about 600° C. and 800° C.;

whereby the combined molar yield of ethylene and vinyl chloride is at least about 80 percent of the ethane reacted.

22 Claims, 1 Drawing Sheet

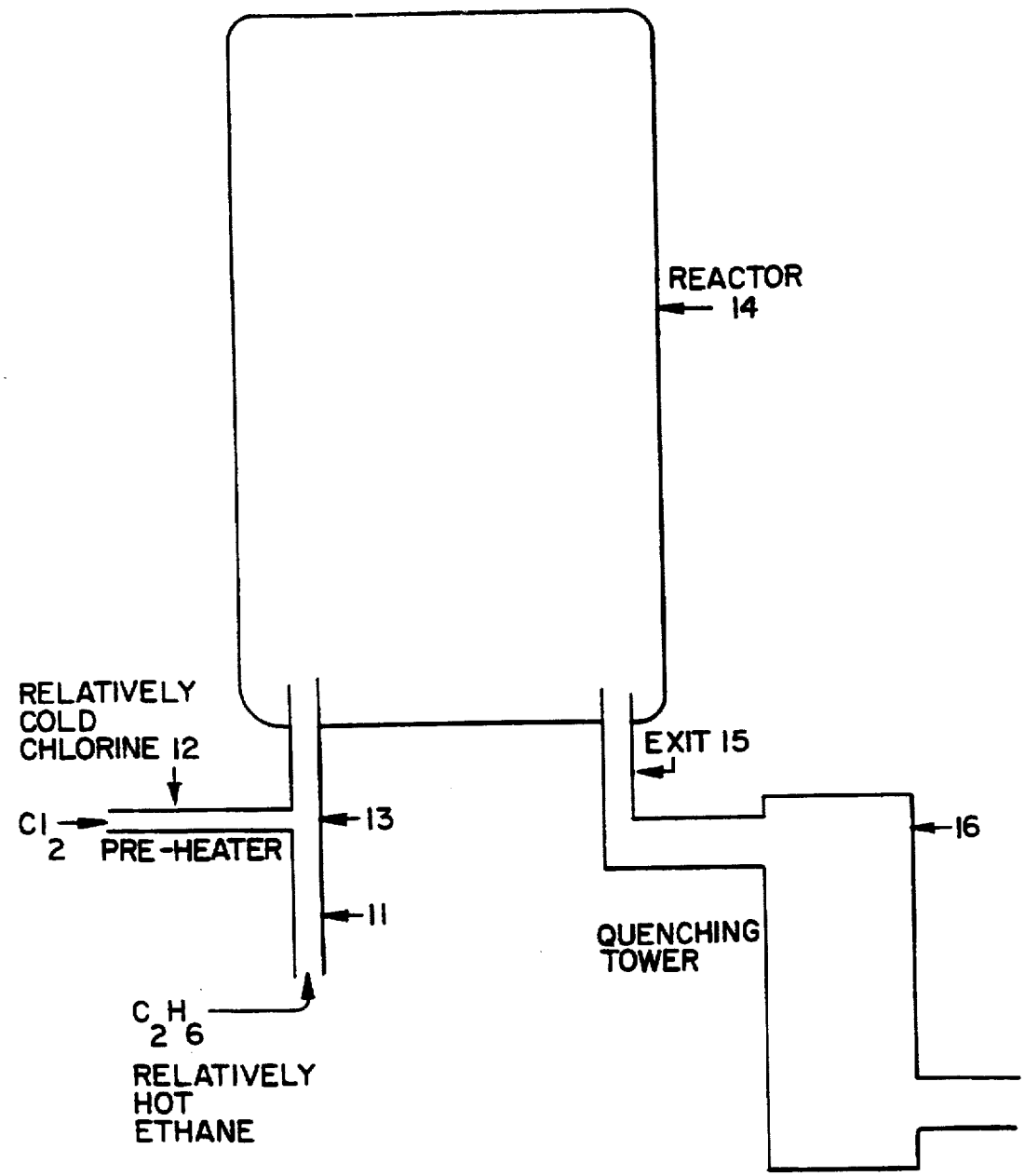

PROCESS FOR THE PRODUCTION OF ETHYLENE AND MIXTURE CONTAINING ETHYLENE

This application is a continuation of application Ser. No. 08/190,434, filed Feb. 2, 1994, now abandoned; which was a continuation of application Ser. No. 08/041,534 filed Apr. 1, 1993, now abandoned; which was a continuation of application Ser. No. 07/622,239 filed Dec. 6, 1990, now abandoned.

BACKGROUND OF THE INVENTION AND PRIOR ART STATEMENT

This invention relates to a process for making ethylene and mixtures of ethylene and vinyl chloride. More particularly, the invention relates to a novel process for making ethylene and mixtures of ethylene and vinyl chloride by the reaction of ethane and chlorine.

Ethylene is a valuable and widely used commodity. Over ten billion pounds of ethylene are consumed each year in the United States alone to make various grades of polyethylene. Another major use of ethylene is as the starting material for making vinyl chloride, which can then be polymerized into polyvinyl chloride (PVC).

In view of the huge quantities of ethylene consumed each year, there is substantial interest in any economical and improved method for making ethylene. At the present time, ethylene is typically made by the high temperature dehydrogenation of ethane and cracking of feedstocks such as naphtha, butane and propane. Such high temperature processes require the expenditure of substantial amounts of energy, which is expensive.

There have been a number of attempts to develop a viable process for the dehydrogenation of ethane or other lower olefinic hydrocarbons by reaction with chlorine or a chlorine-containing compound. As far as we know, none of these prior attempts have resulted in a commercially viable process.

Baehr et al U.S. Pat. No. 2,259,195 discloses a process in which chlorine is used to dehydrogenate paraffinic and olefinic hydrocarbons having 3 to 8 carbon atoms. In this process the chlorine and the hydrocarbon are mixed and reacted in the gas phase at a temperature of 300° to 800° C. Although Baehr et al alleges that the process of that patent is applicable to hydrocarbons of 3 to 8 carbon atoms, all examples of that patent are directed to hydrocarbon of 4 carbon atoms except one example on iso-pentane. And, though Baehr et al at page 2, column 1, lines 1–33, discloses that either or both of the hydrocarbon or chlorine may be preheated, there is no teaching of how this may be done with ethane to result in high selectivity for ethylene and vinyl chloride. In Comparative Example A herein, we show that the procedure of Baehr et al's Example 1, when applied to ethane, would cause almost immediate coking and plugging of the system.

Gorin et al U.S. Pat. No. 2,488,083 shows a process for converting gaseous methane and natural gas to liquid hydrocarbons via alkyl halide intermediary, followed by dehydrohalogenocondensation. The separation of hydrogen chloride from other gaseous materials is shown.

Dirstine et al U.S. Pat. No. 2,628,259 discloses a process for chlorinating ethane to produce vinylidene chloride (1,1-dichloroethylene) and vinyl chloride. This process is conducted at a temperature of 450° C. to 600° C., in the presence of a diluent gas at a chlorine to ethane molar ratio of between 1.9 and 3.0. Though Dirstine et al shows a preheater to be used in starting the operation, his main concern was that his reaction would liberate considerably more heat than can be used and to prevent undesirable consequences he uses the diluent to cool and control the temperature of the reacting mixture (column 4, lines 61–72).

Conrad et al U.S. Pat. No. 2,838,579 discloses a process for the chlorination of ethane to produce chloroethane products such as ethyl chloride, 1,1-dichloroethane or 1,2-dichloroethane, or higher chloroethanes if desired. The process is conducted at high pressure in a temperature range of 300° to 600° C. in the presence of a fluidized bed catalyst consisting of inorganic, carbon coated particles.

Mullineaux et al U.S. Pat. No. 2,890,253 discloses the use of iodine and free oxygen to dehydrogenate saturated hydrocarbons including ethane to yield unsaturated hydrocarbons. There is no disclosure in Mullineaux et al of preheating the feed streams, and in the example showing reaction of iodine with ethane (Example VI, column 10) the amount of ethane reacted was only 40 percent.

Taylor U.S. Pat. No. 3,166,601 discloses a process for the chlorination of ethane to produce unsaturated, chlorinated products. This process is conducted with a substantial excess of chlorine (a molar ratio of chlorine to ethane of 1–4 is maintained), and at a temperature of 600° to 900° C. in the presence of an inert diluent gas.

Carroll et al U.S. Pat. No. 3,173,962 discloses an oxychlorination process for converting alkanes containing 2 to 6 carbon atoms into olefins and chlorinated alkanes which comprises passing a mixture of the alkane, hydrogen chloride, and oxygen or oxygen-containing gas over a catalyst, at a temperature of about 300° to 650° C.

Bajars U.S. Pat. No. 3,207,811 discloses a catalytic process for dehydrogenating aliphatic hydrocarbons of 4 to 6 carbon atoms which comprises heating the aliphatic hydrocarbon with oxygen, and a source of chlorine to a temperature of 450° C. to 1000° C. in the presence of a catalyst.

Riegel U.S. Pat. No. 3,557,229 discloses a catalytic process for the oxychlorination of ethane to produce vinyl chloride, along with ethyl chloride, dichloroethane, ethylene and other compounds. The process contemplates the reaction of ethane, hydrochloric acid and an oxygen source in the presence of a homogeneous catalyst melt.

Beard U.S. Pat. No. 3,558,735 discloses a catalytic oxydehydrogenation process for the production of ethylene in which ethane is reacted with hydrogen chloride and oxygen in the presence of a fluidized copper chloride and rare earth halide catalyst at a temperature of 350° to about 650° C.

Beard U.S. Pat. Nos. 3,658,934; 3,702,311; and 3,862,996 disclose catalytic processes for the production of ethylene and vinyl halide which comprise halodehydrogenating ethane with a halogen, in the presence of an inert gas diluent and a catalyst at a temperature of above 350° C. to about 650° C. to obtain ethylene, oxyhalogenating the ethylene to obtain dihaloethane, and dehydrohalogenating the dihaloethane to obtain the vinyl halide. The very large amount of inert diluent used in the halodehydrogenation step, apparently needed to control the reaction temperature, makes the process relatively inefficient.

Kroenke et al disclose in a series of patents (U.S. Pat. Nos. 4,102,935; 4,119,570; 4,375,569; 4,461,919 and 4,467,127, as well as Magistro U.S. Pat. No. 4,102,936) a process for the oxychlorination of ethane to produce a mixture of ethylene, ethylene dichloride, vinyl chloride, and ethyl chloride. In this process ethane, oxygen, preferably from air, and a chlorine source such as hydrogen chloride, are reacted in the presence of a solid solution catalyst at a temperature from 400° to about 650° C.

Zaidman et al U.S. Pat. No. 4,217,311 discloses a process for the production of vinyl chloride. In this process, a mixture of ethylene and ethane are reacted with chlorine at a temperature of between 300° to 550° C. The chlorine is added at 4 to 6 different points of the reaction zone to lower power consumption and to reduce losses of vinyl chloride due to entrainment.

Li U.S. Pat. No. 4,300,005 discloses a catalytic process for producing monohalogenated olefins and other products by the oxychlorination of 2 to 4 carbon alkanes. In the process, the alkane is reacted with a hydrogen halide and an oxygen source at a temperature of about 400° to 650° C. in the presence of a copper halide/alkali metal phosphate catalyst.

Pyke et al British Patents 2,095,242A and 2,095,245A disclose a catalytic process for producing vinyl chloride by reacting ethane, with a chlorine source and molecular oxygen at a temperature of 275° to 500° C. in the presence of a catalyst.

We are also aware of a copending U.S. patent application Ser. No. 07/488,451, filed Feb. 23, 1990, in the name of one of us, Sidney W. Benson, together with a coinventor, Maja A. Weissman. That application discloses a process for the production of alkenes by the reaction of alkanes with chlorine. The process involves forming a mixture of an alkane (such as ethane) and chlorine, heating the mixture to initiate reaction, and conducting the reaction at a temperature between about 750° K and 1200° K (about 475° C. to 925° C.) to form an alkene (such as ethylene) through the alkylchloride intermediary.

SUMMARY OF THE INVENTION

The present invention provides an efficient process for the production of ethylene or a mixture of ethylene and vinyl chloride, in which some 1,2-dichloroethane (EDC) may also be produced, by reacting chlorine with ethane. The process is characterized by a conversion of ethane per pass through the reactor of at least about 50%, and a combined molar yield of ethylene and vinyl chloride of at least about 80% based on the ethane consumed.

In accordance with this invention, there is provided a process for preparing ethylene or a mixture of ethylene and vinyl chloride by the reaction of ethane and chlorine which comprises:

(a) providing a stream of ethane feed gas and a stream of chlorine feed gas;

(b) preheating either said ethane stream only or both said ethane and chlorine streams;

(c) thoroughly mixing said ethane and chlorine feed gases within about one second and at a molar ratio of ethane to chlorine of at least about 0.9:1.0;

(d) said preheating being sufficient to enable the resultant mixture to have a temperature above the free radical formation temperature for chlorine; and (e) permitting said ethane and chlorine in said mixture to react so that the reacted mixture has a temperature between about 600° C. and 800° C.;

whereby the combined molar yield of ethylene and vinyl chloride is at least about 80 percent of the ethane reacted.

BRIEF DESCRIPTION OF THE DRAWING

FIG. 1 is a schematic diagram of equipment suitable for practicing the process of this invention.

DETAILED DESCRIPTION OF THE INVENTION

It is believed that the conversion of ethane and chlorine to produce ethylene and vinyl chloride results from a series of several intermediate reactions, including:

(1) chlorination of ethane to form ethyl chloride as represented by the equation:

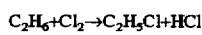

(2) cracking of ethyl chloride to form ethylene as represented by the equation:

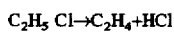

(3) chlorination and dehydrogenation of ethane to form vinyl chloride through a series of reactions which can be represented by the overall equation:

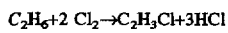

(4) dehydrogenation of ethane to form ethylene, as represented by the equation:

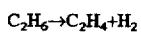

Of these reactions, the chlorination of ethane (reaction (1)) is highly exothermic, generating 28.65 k cal/mole of ethyl chloride formed. The heat of reaction is relied on in the process of this invention to heat the reacting mixture to the desired final temperature of from about 600° C. to about 800° C. Reaction (3) is also exothermic, generating 41 k cal/mole of vinyl chloride formed, and also provides heat to sustain the process of this invention.

Reactions (2) and (4), on the other hand, are endothermic, and require 17.27 k cal/mole of ethylchloride reacted and 32.74 k cal/mole of ethane reacted, respectively. The process of this invention uses the exothermic heat of reaction generated by reaction (1), and possibly (3), to supply heat for reactions (2) and (4).

It is to be understood that the term "the reaction between ethane and chlorine" as used in this application, unless otherwise specifically stated, is intended to refer to the overall effect of all four reactions indicated above.

It is also believed that the reactions for the chlorination of ethane are initiated by the action of free chlorine radicals. The temperature at which thermal dissociation of chlorine takes place to form some free chlorine radicals is generally taken to be about 215° C. to 275° C. and above. See, the two papers presented by William E. Vaughan and Frederick F. Rust at the 99th Meeting of the American Chemical Society in Cincinnati, Ohio, Apr. 8–12, 1940, on The High Temperature Chlorination of Paraffin (and Olefin) Hydrocarbons. See also, Vaughan & Rust, *The High-Temperature Chlorination of Paraffin Hydrocarbons*, 5 J. Org. Chem. 449–71 (1940); and Vaughan & Rust British Patent 542,993 and U.S. Pat. No. 2,249,922. Thus, to initiate the reaction between chlorine and ethane, it is necessary to heat the chlorine above about 215° C., or to use a suitable catalyst and a temperature somewhat below 215° C., or bring about free radical formation by some other means. In the process of the present invention, we prefer to obtain the formation of chlorine free radicals by the use of temperatures above about 215° C.

In addition to the need to bring the chlorine temperature in the reacting mixture to above about 215° C., the reaction of chlorine and ethane is also faced with several other facts that pose conflicting requirements on the reaction. As shown above, reaction (1) is highly exothermic and once initiated, tends to cause the rapid formation of additional free radicals in the chlorine present and thus the complete reaction of the remaining ethane and chlorine. It is also recognized that the ethane and chlorine feed gases must be thoroughly and intimately mixed in order to have the reactions proceed in the desired manner, resulting in high yields of the desired products and avoidance of formation of undesired products. And the rate of heat transfer from a solid surface heat source, such as a heated pipe, to a gaseous mixture, such as chlorine and ethane, is relatively poor, thus making it difficult to rapidly increase the temperature of the gaseous mixture in a relatively short time. Again, to obtain desirable conversion and yield figures, it is preferred that the gaseous mixture leave the reactor at a temperature between about 600° C. and 800° C.

Experience has shown that, at the most preferred molar ratio range of ethane to chlorine, the overall temperature rise in the reactor due to the release of heat of reaction is about 150° to 200° C. Our experience also shows that the feed gas mixture is preferably either initially at about 450° to about 600° C. upon the initiation of the reaction, or additional heat must be transferred to the reacting gaseous mixture during the course of the reaction to produce the desired end temperature for the reacting gaseous mixture.

In summary, a commercially viable non-catalytic reaction between ethane and chlorine appears to be broadly classifiable into two basic processes:

(A) A process in which the ethane and chlorine feed gases are thoroughly mixed before the chlorine therein achieves a temperature of about 215° to 275° C. Such a process is the subject matter of said application Ser. No. 07/488,451. In such a process, the mixing is straightforward, but the heating of the resultant mixture to proper reaction temperatures (both in terms of fast heat transfer and the proper material of construction of the heating surface or vessel) is difficult to control in order to avoid formation of coke and undesirable chlorinated by-products.

(B) A process in which one or both of the feed gas streams, either ethane alone or both ethane and chlorine are preheated before mixing so that the resultant gaseous mixture will have a temperature of at least about the free radical formation temperature for chlorine. Here the initial heat transfer is simpler, but the mixing and additional heat transfer during reaction must be handled in a manner to avoid coking and formation of undesirable chlorinated by-products. This process is the subject matter of the present application.

As indicated above, the process of the present invention contemplates the preheating of either the ethane alone or both ethane and chlorine prior to their mixing, so that the resultant mixture will have a temperature at least about the free radical formation temperature for chlorine. This is accomplished by one of the following embodiments:

(I) A process wherein all necessary heat for the reaction is derived from preheating the reactants and from the exothermic reactions taking place in the reaction zone—and wherein relatively hot ethane (above about 215° C.) is mixed with relatively cold chlorine (below about 215° C.). In this embodiment, the relatively hot ethane will generally be at about 450° to about 600° C., and the relatively cold chlorine will be at ambient temperature to about 180° C., to form a mixture having a temperature between about 400° to about 600° C. In this embodiment, in which the reaction is conducted substantially adiabatically, the use of an efficient mixing technique, to be described below, could result in the substantial simultaneous accomplishment of both thorough mixing of the reactants and the formation of free chlorine radicals in the resultant mixture. By the phrase "the reaction is conducted substantially adiabatically" we mean that the reactants are at such initial temperatures, which together with the heats of reactions that occur (whether endothermic or exothermic), will result in a desired final temperature for the reacting mixture, without the need to add heat to the reacting mixture except perhaps to offset any heat loss to the surroundings.

(II) A process wherein all necessary heat for the reaction is derived from preheating the reactants and from the exothermic reactions taking place in the reaction zone—and wherein hot ethane (above about 215° C.) is mixed with hot chlorine (above about 215° C.) so that upon mixing, the mixture will react substantially instantaneously. Due to the presence of the free radicals in that hot chlorine, the mixing of the reactants should take place essentially at the front end or inside of the reaction zone so that the reaction can be permitted to commence instantaneously. In this embodiment, it is contemplated that the reaction will also be conducted substantially adiabatically, so that the mixture of the hot chlorine and ethane should have a temperature of about 400° to about 600° C. to achieve a final temperature of the reacting mixture of about 600° to about 800° C.

(III) This embodiment contemplates the preheating of only ethane so that a mixture of ethane and chlorine will have a temperature between about 215° C. and about 400° C.—so that some additional heat input to the reacting mixture is necessary in order to achieve the desired final temperature of the reacting mixture of between about 600° to about 800° C. This is a non-adiabatic embodiment of the process of the invention, and the heat input to the reacting mixture is most conveniently provided by heat transfer in the reaction zone.

In practicing the process of the present invention, specific temperatures of the ethane and chlorine feed gases are not narrowly critical. We have found that one of the important parameter of the process is the final temperature of the reacting mixture leaving the reaction zone. In general, that final temperature should be within the range of from about 600° C. to about 800° C. The production of ethylene falls at temperatures below about 600° C. and undesirable by-product formation increases above about 800° C. A final temperature of the reacting mixture of from about 650° C. to about 750° C. is particularly preferred.

The final temperature of the reacting mixture is largely determined by several factors: the initial temperature of the mixture of ethane and chlorine prior to any substantial reaction between the ethane and chlorine; the molar ratio of ethane to chlorine used, as well as the presence or absence of any diluent, which together largely determine the amount of heats of reactions liberated in the reaction zone; and the amount of heat that is transferred to the mixture in the reaction zone. Thus, at a given molar ratio of ethane to chlorine, without the presence of any diluent, and conducting the reaction adiabatically, the final reaction temperature is essentially determined by the initial ethane and chlorine mixture and the heats of reactions liberated in the reaction zone. In general, we have found that the temperature rise for the reacting mixture in the reaction zone due to the heats of reactions lies in the range of about 150° C. to somewhat above 200° C.

As indicated above, the molar ratio of ethane to chlorine to be used in the process of the present invention is at least about 0.9:1.0. The particular ratio chosen is a function of the products desired. Although ethylene and vinyl chloride are always produced by the process of this invention, the relative proportions of the two products, as well as other products formed, will vary depending upon the ratio of ethane to chlorine, with the yield of vinyl chloride decreasing with increasing ratio of ethane to chlorine.

If too little chlorine is used, the reaction will produce few by-products and little vinyl chloride, but will leave a large amount of ethane unreacted. In such a case, more elaborate product separation will be required to recover the ethylene produced and recycle the unreacted ethane. On the other hand, use of an excessive quantity of chlorine will lead to polychlorinated products, other side products, and carbon formation. In general, good results are obtained with a molar ratio of ethane to chlorine in the range of from about 1:1.0 to about 4:1.0, preferably in the range of from about 1.1:1.0 to about 2:1.0, and most preferably from about 1.3:1.0 to about 1.6:1.0.

The presence of an inert diluent in the relatively cold chlorine stream can be useful to moderate the reaction by absorbing some of the heat generated by exothermic reactions, thus minimizing local hot spots. As an alternative, relatively cold ethane can be mixed with relatively cold chlorine before mixing with the relatively hot ethane, in order to achieve the same result. In either event, it is important that the gas added to the chlorine stream does not absorb too much heat, and thereby interfere with the endothermic reactions. Using known thermodynamic parameters of the gases involved, one skilled in the art can readily calculate permissible levels of inert diluent or ethane which may be added to the chlorine stream without interfering with the reaction.

Another key aspect of the process of this invention is ensuring that the ethane and chlorine are intimately and thoroughly mixed substantially instantaneously, i.e., thoroughly mixed within about 1 second. Such rapid mixing is desired to avoid the prolonged presence of localized excess concentrations of chlorine at a temperature above 215° C., which may lead to reactions forming polychlorinated compounds, acetylene, and, in extreme cases, even carbon.

Such rapid intimate mixing may be accomplished by suitable means. We have developed a means for achieving such mixing by flowing ethane under turbulent conditions through a conduit and introducing the chlorine, also in turbulent flow, into the ethane stream. In a preferred embodiment shown in FIG. 1, the chlorine is introduced into the ethane stream through a second conduit perpendicular to, and communicating with, the conduit carrying the ethane.

It has also been found that, in order to ensure the thorough mixing, the linear velocity of the chlorine stream should be greater than that of the ethane stream in accordance with the teachings of Cozewith & Busko, *Design Correlations For Mixing Tees*, 18 Ind. Eng. Chem. Res. 1521–1530 (1989). In the embodiment shown in FIG. 1, in which a single stream of chlorine is injected into the ethane stream, we have found that a linear velocity of chlorine of about 1.7 to about 3 times the linear velocity of ethane to be suitable.

When a device in the form shown in FIG. 1 is used, we prefer to use a mixing zone having a length about five to ten times the diameter of the conduit containing the mixture. Longer or shorter mixing zones can be used. When such mixing conditions are maintained, we have found that rapid and intimate mixing may be accomplished in 0.1 second or less, preferably about 0.01 second or less. Although some reaction may occur in the mixing zone, we believe that no substantial amount of reaction takes place in the mixing zone in such a short time because heat must be transferred from the ethane stream to the chlorine, free radicals will have to be formed by the heated chlorine, and the free radicals will then have to react with the ethane present.

In embodiment (II) of the process of this invention, described above, hot chlorine (above about 215° C.) is mixed with hot ethane for adiabatic reaction within the reaction zone. In that embodiment, the free chlorine radicals already present in the relatively hot chlorine will react substantially instantaneously upon contact with ethane. Therefore, the mixing of the hot chlorine and hot ethane preferably should take place at the entrance to the reaction zone, or inside of it, so that the reaction can safely proceed.

As noted above, the mixture of ethane and chlorine is introduced into an inert reaction zone, which can be simply an extension of the conduit containing the reaction mixture, i.e., a tubular reactor, or can be a reactor of larger cross-section.

When the reaction is conducted in a tubular reactor of relatively small diameter, such that plug flow is obtained, the temperature of the reaction mixture will vary in the absence of heating or cooling. Initially the temperature will increase due to the exothermic nature of reaction (1). It then will fall as endothermic reactions, such as reactions (2) and (4), are initiated. The reactor should be insulated or provided with heating or cooling means as needed to maintain the reaction temperature within the range of from about 600° C. to about 800° C.

In a tubular reactor where there is a plug flow, heating will not be required in the initial section where exothermic reaction (1) is taking place. However, heating may be desirable at later stages where endothermic reactions would otherwise reduce reaction temperature.

It is preferred, however, to employ a reactor of large diameter, such as a spherical or cylindrical reactor, so that plug flow is minimized and intimate mixing, including backmixing, of the ethane-chlorine feed mixture with reacted gasses formed in the reactor is achieved. In this way, the exothermic heat of, e.g., reaction (1), may be more efficiently used to drive the endothermic reactions. Moreover, the rapid mixing of the hot ethane/chlorine mixture with products in the reactor prevents the temperature within the reaction zone from going too high. It is preferred that the highest localized temperature in the reactor not exceed 800° C. for a significant period of time. The local temperature may exceed 800° C. if the period of high temperature is short, on the order of 1 second or so.

As an alternative to using a single reactor, in Embodiment I of the process of this invention may be conducted in two or more reactors in series, in which all the ethane to be used is introduced into the first reactor, but only a portion of chlorine is mixed with the ethane feed. The reaction stream from the first reactor then is fed to the second reactor, and more of the chlorine is mixed with the hot reaction stream before introduction into the second reactor. If there are more than two reactors, the reaction product from each reactor is introduced into the next reactor along with more chlorine. The total amount of chlorine introduced in all reactors is such that the molar ratio of ethane to chlorine is at least about 0.9:1.

The advantage of introducing chlorine in two or more stages, rather than one, is that it allows for easier mixing of the chlorine with the ethane in the first mixing step, and leaves less chance for the side product formation which can result from poor mixing and localized high chlorine concentrations. As noted above, such poor mixing can lead to polychlorinated compounds, acetylene, and even carbon formation. In the second or subsequent reactors, the problems of poor mixing are again lessened because the ethane is now diluted with the reacted gases produced in the prior reactor.

The method used to mix ethane prior to the first reactor are suitable for mixing chlorine with reactant gases prior to the second or subsequent reactor. The proportion of chlorine introduced prior to the first reactor may be varied over a fairly wide range, but must be sufficient so that the temperature in the reactor quickly rises to above about 600° C. On the other hand, the amount of chlorine introduced in the first reactor should not be so high that the reaction is substantially complete before the gasses are admitted to the second reactor.

In order to achieve the purposes of this invention, it is important that the inner surface of the reactor be inert. Most metallic reactors cause side reactions which lead to carbon formation. We have found that quartz, silicon carbide, alumina, and graphite linings are suitable. However, one skilled in the art could, without undue experimentation, find other inert materials which would be suitable for the lining of a reactor for this process.

A catalyst is not required for conducting the process of this invention. However, dehydrohalogenation catalysts such as activated carbon and alumina may be used if desired.

In a preferred embodiment, the process of this invention is conducted in a substantially adiabatic manner. That is, to the exent possible, the desired reaction temperature is sustained by the exothermic heat of reaction (1) and other exothermic reactions. Accordingly, it is desired that the reactor be insulated to avoid loss of heat to the surroundings. Where this is not possible, heat may be added to compensate for heat loss, and thereby achieve substantially adiabatic conditions within the reaction zone.

In conducting a substantially adiabatic reaction, it is preferred that the reactor have a configuration such that the ratio of surface area to volume is low, in order to minimize the heat loss from the reactor and provide the best opportunity of retaining the heat of reaction. Spherical reactors, and cylindrical reactors in which the length is approximately equal to the diameter, are examples of reactors with a low ratio of surface area to volume. Those skilled in the art can readily conceive of other shapes which will provide a low surface area to volume ratio.

An example of a suitable reactor is shown in FIG. 1. As shown in FIG. 1, relatively hot ethane in turbulent flow is introduced through a first conduit 11, and relatively cold chlorine is introduced through perpendicular second conduit 12, and mixed at 13. The resulting mixture of ethane and chlorine emerges from mixing zone 13 and enters the reactor 14. The distance between mixing point 13 and the entrance to reactor 14 is preferably equal to 3 times the diameter of conduit 11. The velocity of the gasses entering reactor 14 is high enough that substantially uniform mixing of feed and reaction products occurs in reactor 14. The reaction gasses are removed through exit conduit 15, and fed to quenching tower 16.

The reactant gasses produced by the process of this invention contain vinyl chloride, hydrogen chloride, ethylene, unreacted ethane, and some hydrogen. The reactant gas stream may be readily fractionated by methods well-known to those skilled in the art, to separate the various components, but this is not necessary. For example, the hydrogen chloride and the ethylene may be processed together to yield 1,2-dichloroethane and vinyl chloride. Oxychlorination reactions are known, in which ethylene, hydrogen chloride and an oxygen source (generally air or pure oxygen) are reacted to form vinyl chloride, as represented by the equations:

$$C_2H_4 + 2HCl + 1/2O_2 \longrightarrow C_2H_4Cl_2 + H_2O$$

$$C_2H_4Cl_2 \xrightarrow{\Delta} C_2H_3Cl + HCl$$

If the stream of product gasses does not contain an appropriate balance of ethylene and hydrogen chloride, one or the other reactant may be added, or alternatively, removed. Such reactions are usually conducted at a temperature in the range of from about 225° C. to about 250° C. over a catalyst, such as copper chloride on alumina. The product of this reaction is 1,2-dichloroethane, which may be thermally cracked to yield vinyl chloride.

The following examples, unless indicated otherwise, illustrate specific embodiments of the invention, but should be construed as merely illustrative, and not limiting of the present invention.

EXAMPLE 1

Ethane heated at 510° C. was fed through a 10 mm ID tube at a rate of 31 l/min. Chlorine gas heated at 170° C. was injected perpendicularly into the ethane stream through a 4 mm ID tube communicating with the ethane tube, at a rate of 15.5 l/min. The mole ratio of ethane to chlorine was 1.78:1 and the linear velocities of ethane and chlorine at the point of mixing were 45.5 ft/sec and 79.7 ft/sec, respectively.

The resulting mixture was passed through a 30 mm long segment of the 10 mm ID tube and then introduced into a tubular reactor having an internal diameter of 8 cm, a length of 140 cm, and made of about 0.25 cm thick quartz tube. Heat was supplied to the reactor to make up for heat losses, and thereby maintain substantially adiabatic conditions, as indicated by maintenance of the temperature of the exterior surface of the middle of the reactor (the so-called "mid-skin temperature") at about 685° C. Residence time was about 2 seconds.

The reaction product was analyzed and it was found that ethane conversion was 57.5%, and product yields, based upon ethane consumption, were as set forth below.

| Product | Yield, mole % |
|---|---|
| Ethylene | 79.3 |
| Vinyl Chloride | 13.5 |
| Dichloroethylenes | 0.37 |
| Ethyl Chloride | 2.3 |
| Acetylene | 1.2 |

Thus, the combined yield of ethylene and vinyl chloride was 92.8%, based upon the amount of ethane consumed.

EXAMPLE 2

The procedure described in Example 1 was repeated, except that the ethane flow rate was reduced to 29 l/min and the chlorine flow rate was increased to 17 l/min, resulting in an ethane to chlorine mole rate of 1.54:1. Conversion of ethane increased to 66.9%, and the yield of vinyl chloride increased slightly.

| Product | Yield, mole % |
|---|---|
| Ethylene | 77.0 |
| Vinyl Chloride | 16.3 |
| Dichloroethylenes | 0.53 |
| Ethyl Chloride | 0.96 |
| Acetylene | 1.3 |

The combined yield of ethylene and vinyl chloride was 93.3%.

EXAMPLE 3

The procedure of Example 1 was repeated, except that the ethane flow rate was further reduced to 27 l/min and chlorine flow rate was increased to 18.5 l/min, resulting in an ethane to chlorine mole ratio of 1.3:1. Ethane conversion increased to 73.6%, and product yields were as follows.

| Product | Yield, mole % |
| --- | --- |
| Ethylene | 74.1 |
| Vinyl Chloride | 17.6 |
| Dichloroethane | 0.68 |
| Dichloroethylene | 0.62 |
| Ethyl Chloride | 0.64 |
| Acetylene | 2.6 |

The combined yield of ethylene and vinyl chloride was 91.7%.

EXAMPLE 4

Ethane heated at 565° C. was passed through a 7 mm ID tube at a rate of 24 l/min. Chlorine gas at room temperature was injected at a rate of 14 l/min perpendicularly into the ethane stream through a 2.2 mm ID tube communicating with the ethane tube. The mole ratio of ethane to chlorine was 1.6:1. The resulting mixture was introduced into the same reactor as Example 1 and reacted for about 3 seconds. Heat was supplied to the reactor to make up for heat loss, as indicated by maintaining a mid-skin temperature of about 700° C.

Analysis of the product stream showed an ethane conversion of 61.4% and the following yields of reaction products:

| Product | Yield, mole % |
| --- | --- |
| Ethylene | 84.3 |
| Vinyl Chloride | 11.0 |
| Dichloroethane | 0.1 |
| Dichloroethylenes | 0.05 |
| Ethyl Chloride | 0.75 |
| Acetylene | 0.71 |

The combined yield of ethylene and vinyl chloride was 95.3%.

The process was repeated twice. In the first repeat, only partial compensation was made for heat loss, as indicated by the reactor mid-skin temperature of 600° C. In the second, no attempt was made to compensate for heat loss at all, and the reactor mid-skin temperature fell to 445° C.

The results of these three experiments are summarized in the following table.

| | Experiment No. | | |
| --- | --- | --- | --- |
| | A | B | C |
| Reaction Conditions | | | |
| Ethane Feed Rate, l/min | 23 | 24 | 24 |
| Chlorine Feed Rate, l/min | 13.2 | 13.6 | 14 |
| Ethane/Chlorine Mole Ratio | 1.6:1 | 1.56:1 | 1.5:1 |
| Compensation For Heat Loss | Full | Partial | None |
| Mid-skin Temperature, °C. | 701 | 600 | 445 |
| Results | | | |
| Ethane Conversion, % | 61.4 | 60.1 | 61.5 |
| Yields, mole % | | | |
| Ethylene | 84.3 | 71.5 | 49.2 |
| Vinyl Chloride | 11.0 | 10.9 | 11.4 |
| Dichloroethane | 0.1 | 0.1 | 0.11 |
| Dichloroethylenes | 0.05 | 0.1 | 1.2 |

-continued

| | Experiment No. | | |
| --- | --- | --- | --- |
| | A | B | C |
| Ethyl Chloride | 0.75 | 14.9 | 35.9 |
| Acetylene | 0.71 | 0.0 | 0.0 |

We believe that maintenance of a temperature of the exiting gas stream from the reactor of about 685° C. through the use of substantially adiabatic conditions resulted in high ethylene yields and low yields of ethyl chloride. When, however, the reaction temperature declined due to heat losses to the atmosphere, the yield of ethylene decreased and the yield of ethyl chloride correspondingly increased.

Comparative Example A

This example was intended to duplicate the experimental conditions given in Example 1 of U.S. Pat. No. 2,259,195, except that ethane was substituted for the butane used in the patent example. Sixty l/hour of ethane and 120 l/hour of chlorine were premixed in a 2.2 mm ID Teflon tube which was 50 cm long. The mixture was passed through a 2 mm quartz capillary tube against a frontal perforated plate heated externally by an electric furnace. The resulting reaction mixture passed through an air-cooled section and a water-cooled exchanger. The frontal plate was arranged in a 15 mm inside diameter quartz tube. The skin temperature of the tube was measured. Reactor skin temperatures of 300°, 600°, and 800° C. were tested. At all temperatures tested, large amounts of carbon were formed. In fact, carbon formation was so severe that in every case the reaction tube was plugged with carbon less than a minute after gas flows were stabilized. Because of the short operation time, gas chromatographic analysis could not be performed to determine what other products, besides carbon, were formed in the reaction.

We claim:

1. A process for preparing ethylene or a mixture of ethylene and vinyl chloride by the reaction of ethane and chlorine which comprises:

(a) providing a stream of ethane feed gas and a stream of chlorine feed gas;

(b) preheating either said ethane stream only or both said ethane and chlorine streams to temperatures sufficient for the resultant mixture to have a temperature above 215° C. allowing the formation of free radicals from chlorine;

(c) thoroughly mixing said ethane and chlorine feed gases at a molar ratio of ethane to chlorine of at least about 0.9:1.0 within less than one second to avoid substantial coking and formation of undesired by-products;

(d) adjusting the final temperature of the reacting gaseous mixture in the reaction zone to between about 600° C. and about 800° C.; and (e) selecting the residence time in the reaction zone such that the combined molar yield of ethylene and vinyl chloride is at least about 80% of the ethane and ethylene predominates in the products reacted.

2. A process according to claim 1 wherein the final temperature of the reacting gaseous mixture is adjusted to between about 600° C. and about 800° C. by selecting (a) the initial temperature of the mixture of ethane and chlorine prior to any substantial reaction between the ethane and chlorine;

(b) the molar ratio of ethane to chlorine used;

(c) the presence or absence of any diluent; and (d) the amount of heat that is transferred to the mixture in the reaction zone.

3. A process according to claim 1 or 2 wherein the reaction zone for said mixture of ethane and chlorine is well insulated to provide for heat conservation so that the reaction may be conducted substantially adiabatically.

4. A process according to claim 1 wherein said preheating enables said resultant mixture to have a temperature between about 400° C. and about 550° C., and wherein heat is transferred to the reacting mixture so that the reacted mixture has a temperature between about 600° C. and about 800° C.

5. A process according to claim 3 wherein the molar ratio of ethane to chlorine is between about 1.1:1.0 to about 2.0:1.0.

6. A process according to claim 3 wherein the molar ratio of ethane to chlorine is between about 1.3:1.0 to about 1.6:1.0, and wherein said reacted mixture has a temperature between about 650° C. and about 750° C.

7. A process according to claim 1 wherein said mixture is permitted to react in a reaction zone, and wherein said mixture has a residence time in said reaction zone at least about 0.5 second.

8. A process according to claim 7 wherein said residence time is about 1 to about 10 seconds.

9. A process according to claim 7 wherein said residence time is about 4 to about 6 seconds.

10. A process according to claim 1 further comprising providing a catalyst to promote the reaction between said ethane and chlorine.

11. A process according to claim 1 further comprising a diluent in said mixture.

12. A process according to claim 11 wherein said diluent is an inert diluent.

13. A process according to claim 11 wherein said diluent is ethane.

14. A process according to claim 1 wherein said ethane and chlorine feed gases are thoroughly mixed by introducing the chlorine at several different locations for mixing with the ethane stream.

15. A process according to claim 1 wherein said ethane and chlorine are reacted in an inert reaction zone made of a material selected from quartz, silicon carbide, alumina, and graphite.

16. A process according to claim 1 further comprising reacting the ethylene and hydrogen chloride produced from the reaction of ethane and chlorine with an oxygen source to produce dichloroethane.

17. A process according to claim 16 further comprising heating said dichloroethane to produce vinyl chloride.

18. A process according to claim 1 wherein said mixing of the ethane and chlorine is accomplished by introducing said ethane stream and said chlorine stream into a mixing zone at an angle of substantially about 90° to each other.

19. A process according to claim 1 wherein said mixing of the ethane and chlorine is accomplished by providing a chlorine stream having a velocity higher than the velocity of the ethane stream.

20. A process for preparing ethylene or a mixture of ethylene and vinyl chloride by the reaction of ethane and chlorine which comprises:

(a) providing a stream of ethane feed gas and a stream of chlorine feed gas;

(b) preheating either said ethane stream only or both said ethane and chlorine streams to temperatures sufficient for the resultant mixture to have a temperature above 215° C. allowing the formation of free radicals from chlorine;

(c) thoroughly mixing said ethane and chlorine feed gases at a molar ratio of ethane to chlorine of at least about 0.9:1.0 within less than one second to avoid substantial coking and formation of undesired by-products;

(d) adjusting the final temperature of the reacting gaseous mixture in the reaction zone to between about 600° C. and about 800° C.;

(e) permitting said ethane and chlorine in said mixture to react in the essential absence of a diluent; and (f) selecting the residence time in the reaction zone such that the combined molar yield of ethylene and vinyl chloride is at least about 80% of the ethane and ethylene predominates in the products reacted.

21. A process for preparing ethylene or a mixture of ethylene and vinyl chloride by the reaction of ethane and chlorine which comprises:

(a) providing a stream of ethane feed gas and a stream of chlorine feed gas;

(b) preheating either said ethane stream only or both said ethane and chlorine streams to temperatures sufficient for the resultant mixture to have a temperature above 215° C. allowing the formation of free radicals from chlorine;

(c) thoroughly mixing said ethane and chlorine feed gases at a molar ratio of ethane to chlorine of at least about 0.9:1.0 within less than one second to avoid substantial coking and formation of undesired by-products;

(d) adjusting the final temperature of the reacting gaseous mixture in the reaction zone to between about 600° C. and about 800° C.;

(e) permitting said ethane and chlorine in said mixture to react in the essential absence of a diluent and a catalyst; and (f) selecting the residence time in the reaction zone such that the combined molar yield of ethylene and vinyl chloride is at least about 80% of the ethane and ethylene predominates in the products reacted.

22. A process according to claim 1 or 2 wherein the temperature of the chlorine stream just prior to its mixing with the ethane stream is below 215° C. and thereby below the temperature allowing the formation of free radicals from the chlorine.

* * * * *